United States Patent [19]

Oku et al.

[11] Patent Number: 5,250,528
[45] Date of Patent: Oct. 5, 1993

[54] NEW AMINOPIPERAZINE DERIVATIVES

[75] Inventors: Teruo Oku, Tsukuba; Eishiro Todo, Toyonaka; Yoshihiro Yokota; Hiroshi Kayakiri, both of Tsukuba; Masashi Hashimoto, Tokyo, all of Japan

[73] Assignee: Fujisawa Pharmaceutical Co., Ltd., Osaka, Japan

[21] Appl. No.: 957,759

[22] Filed: Oct. 8, 1992

Related U.S. Application Data

[63] Continuation of Ser. No. 671,797, Apr. 2, 1991, abandoned.

[30] Foreign Application Priority Data

Aug. 2, 1989 [GB] United Kingdom ............... 8917687

[51] Int. Cl.$^5$ ............... A61K 31/495; C07D 295/32; C07D 409/06; C07D 403/06
[52] U.S. Cl. ............... 514/252; 514/253; 514/255; 544/121; 544/179; 544/215; 544/238; 544/357; 544/295; 544/360; 544/363; 544/365; 544/366; 544/367; 544/368; 544/369; 544/370; 544/371; 544/372; 544/373; 544/376; 544/379; 544/382
[58] Field of Search ............... 544/382, 379; 514/252, 514/255

[56] References Cited

U.S. PATENT DOCUMENTS

| 3,200,120 | 8/1965 | Lovell | 544/375 |
| 3,200,121 | 8/1965 | Lovell | 544/382 |
| 4,267,175 | 5/1981 | Watts | 544/382 |
| 4,857,644 | 8/1989 | Abou-Gharbia | 544/382 |
| 4,895,841 | 1/1990 | Sugimoto et al. | 514/212 |

FOREIGN PATENT DOCUMENTS

| 89900 | 9/1983 | European Pat. Off. | |
| 299493 | 1/1989 | European Pat. Off. | |
| 3919175 | 9/1964 | Japan | |
| 106570 | 5/1986 | Japan | |
| 722627 | 1/1955 | United Kingdom | 544/382 |
| 996253 | 6/1965 | United Kingdom | |
| 2162843 | 2/1986 | United Kingdom | |

OTHER PUBLICATIONS

Willecome, *Ann. Chim.*, pp. 405–428 (1969).
Bulacinski et al, vol. 108, No. 37783 (1988).

*Primary Examiner*—Emily Bernhardt
*Attorney, Agent, or Firm*—Oblon, Spivak, McClelland, Maier & Neustadt

[57] ABSTRACT

This invention relates to new aminopiperazine derivatives having the potentiation of the cholinergic activity and represented by the general formula [I]:

$$R^1-A-N\underset{\diagdown\_\_\diagup}{\overset{\diagup\overline{\phantom{xx}}\diagdown}{}}N-\underset{\underset{R^2}{|}}{N}-Y-R^3 \quad [I]$$

wherein
$R^1$ is lower alkyl, aryl, ar(lower)alkoxy or a heterocyclic group, each of which may be substituted with halogen,
$R^2$ is hydrogen or lower alkyl,
$R^3$ is cyclo(lower)alkyl, aryl or ar(lower)-alkyl, each of which may be substituted with halogen,
A is $$-\overset{\overset{\displaystyle O}{\|}}{C}-,\ -SO_2-$$

or lower alkylene, and
Y is $$-\overset{\overset{\displaystyle O}{\|}}{C}-,\ -SO_2-\ \text{or}\ -\overset{\overset{\displaystyle O}{\|}}{C}NH-,$$

and pharmaceutically acceptable salts thereof, to processes for the preparation thereof and to a pharmaceutical composition comprising the same.

8 Claims, No Drawings

NEW AMINOPIPERAZINE DERIVATIVES

This application is a Continuation of application Ser. No. 07/671,797, filed on Apr. 2, 1991, now abandoned.

TECHNICAL FIELD

This invention relates to new aminopiperazine derivatives and pharmaceutically acceptable salts thereof which are useful as a medicament.

BACKGROUND ART

Some piperazine derivatives have been known as useful anti-amnesia agents, for example, in G.B. Patent Application Publication No. 2 162 843 and EP Patent Application Publication No. 299 493, but the N-substituents of piperazine ring in these compounds do not contain amino group while our compounds are N-aminopiperazine derivatives.

DISCLOSURE OF INVENTION

This invention relates to new aminopiperazine derivatives and pharmaceutically acceptable salts thereof.

More particularly, it relates to new aminopiperazine derivatives and pharmaceutically acceptable salts thereof which have the potentiation of the cholinergic activity, to processes for the preparation thereof, to a pharmaceutical composition comprising the same, and to a method for the treatment of disorders in the central nervous system for human beings, and more particularly to method for the treatment of amnesia, dementia, senile dementia and the like.

One object of this invention is to provide new and useful aminopiperazine derivatives and pharmaceutically acceptable salts thereof which possess the potentiation of the cholinergic activity.

Another object of this invention is to provide processes for preparation of said aminopiperazine derivatives and salts thereof.

A further object of this invention is to provide a pharmaceutical composition comprising, as an active ingredient, said aminopiperazine derivatives and pharmaceutically acceptable salt thereof.

Still further object of this invention is to provide a therapeutic method for the treatment of disorders in the central nervous system for human beings, and more particularly of amnesia, dementia, senile dementia and the like, using said aminopiperazine derivatives and pharmaceutically acceptable salts thereof.

The aminopiperazine derivatives of this invention are new and can be represented by the following general formula [I]:

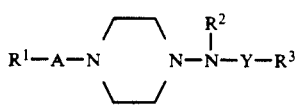

wherein
R$^1$ is lower alkyl, aryl, ar(lower)alkoxy or a heterocyclic group, each of which may be substituted with halogen,
R$^2$ is hydrogen or lower alkyl,
R$^3$ is cyclo(lower)alkyl, aryl or ar(lower)alkyl, each of which may be substituted with halogen,
A is

or lower alkylene, and
Y is

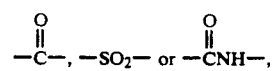

and pharmaceutically acceptable salts thereof.

The object compound [I] or its salt can be prepared by processes as illustrated in the following reaction schemes.

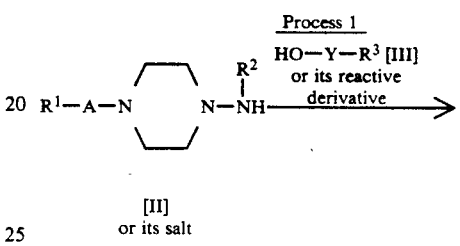

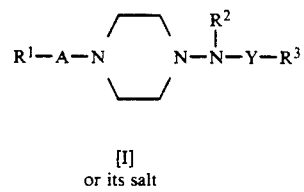

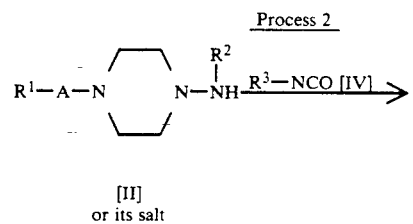

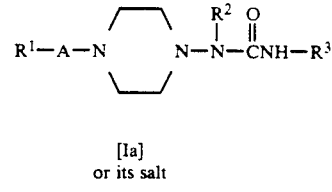

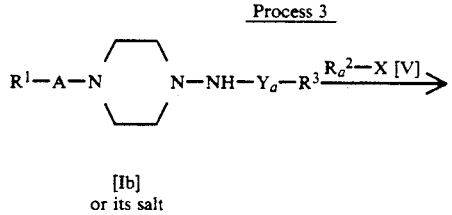

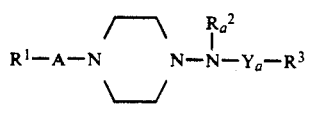

wherein $R^1$, $R^2$, $R^3$, A and Y are each as defined above, $R^2_a$ is lower alkyl, $Y_a$ is

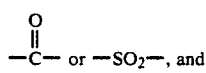

X is an acid residue.

In the above and subsequent description of the present specification, suitable examples of the various definitions to be included within the scope of the invention are explained in detail in the following.

The term "lower" is intended to mean a group having 1 to 6 carbon atom(s), unless otherwise provided.

Suitable "lower alkyl" may be a straight or branched one such as methyl, ethyl, propyl, isopropyl, butyl, isobutyl, tert-butyl, pentyl, hexyl, or the like, in which preferable one is methyl.

Suitable "aryl" may be phenyl, naphthyl, tolyl, xylyl, mesityl, cumenyl, and the like, in which preferable one is phenyl or naphthyl.

Suitable "ar(lower)alkoxy" may be benzyloxy, phenethyloxy, phenylpropoxy, benzhydryloxy, trityloxy and the like.

Suitable "heterocyclic group" may include saturated or unsaturated, monocyclic or polycyclic one containing at least one hetero atom such as nitrogen atom, oxygen atom or sulfur atom.

The preferred examples of thus defined "heterocyclic group" may be unsaturated, 3 to 8-membered, more preferably 5 or 6-membered heteromonocyclic group containing 1 to 4-nitrogen atom(s), for example, pyrrolyl, imidazolyl, pyrazolyl, pyridyl, pyridyl N-oxide, dihydropyridyl, tetrahydropyridyl, pyrimidyl, pyrazinyl, pyridazinyl, triazinyl, triazolyl, tetrazinyl, tetrazolyl, etc.;

unsaturated, condensed heterocyclic group containing 1 to 5 nitrogen atom(s), for example, indolyl, isoindolyl, indolizinyl, benzimidazolyl, quinolyl, isoquinolyl, indazolyl, benzotriazolyl, etc.;

unsaturated, 3 to 8-membered heteromonocyclic group containing 1 to 2 oxygen atom(s) and 1 to 3 nitrogen atom(s), for example, oxazolyl, isoxazolyl, oxadiazolyl, etc.;

saturated, 3 to 8-membered heteromonocyclic group containing 1 to 2 oxygen atom(s) and 1 to 3 nitrogen atom(s), for example, morpholino, sydnonyl, etc.;

unsaturated, condensed heterocyclic group containing 1 to 2 oxygen atom(s) and 1 to 3 nitrogen atom(s), for example, benzoxazolyl, benzoxadiazoly, etc.;

unsaturated, 3 to 8-membered heteromonocyclic group containing 1 to 2 sulfur atom(s) and 1 to 3 nitrogen atom(s), for example, thiazolyl, isothiazolyl, thiadiazolyl, etc.;

unsaturated, 3 to 8-membered heteromonocyclic group containing 1 to 2 sulfur atom(s), for example, thienyl, etc.;

unsaturated, condensed heterocyclic group containing 1 to 2 sulfur atom(s) and 1 to 3 nitrogen atom(s), for example, benzothiazolyl, benzothiadiazolyl, etc.;

unsaturated, 3 to 8-membered heteromonocyclic group containing an oxygen atom, for example, furyl etc.;

unsaturated, condensed heterocyclic group containing 1 to 2 sulfur atom(s), for example, benzothienyl, etc.;

unsaturated, condensed heterocyclic group containing 1 to 2 oxygen atom(s), for example benzofuranyl, etc.; or the like.

Suitable "cyclo(lower)alkyl" may be cyclopropyl, cyclobutyl, cyclopentyl, cyclohexyl, and the like.

Suitable "ar(lower)alkyl" may be benzyl, phenethyl, phenylpropyl, benzhydryl, trityl, and the like.

Suitable "lower alkylene" may be methylene, ethylene, propylene, pentamethylene, hexamethylene, and the like.

Suitable "acid residue" may include halogen (e.g. fluorine, chlorine, bromine, iodine, arenesulfonyloxy (e.g., benzenesulfonyloxy, tosyloxy,etc, lower alkanesulfonyloxy (e.g. mesyloxy, ethanesulfonyloxy, etc.) and the like.

The above-mentioned "lower alkyl", "aryl", "ar(-lower)alkoxy", "heterocyclic group", "cyclo(lower)alkyl" and "ar(lower)alkyl" may be substituted with halogen [e.g. fluorine, chlorine, bromine and iodine].

Suitable pharmaceutically acceptable salts of the object compound [I]are conventional non-toxic salts and include acid addition salt such as an inorganic acid addition salt [e.g. hydrochloride, hydrobromide, sulfate, phosphate, etc.], an organic acid addition salt [e.g. formate, acetate, trifluoroacetate, maleate, tartarate, methanesulfonate, benzenesulfonate, toluenesulfonate, etc.], a salt with an amino acid [e.g. aspartic acid salt, glutamic acid salt, etc.]and the like.

The processes for preparing the object compound [I] are explained in detail in the following.

Process 1

The compound [I] or its salt can be prepared by reacting a compound [II] or its salt with a compound [III] or its reactive derivative at the carboxy or sulfo group.

Suitable salts of the compound [II]may be the same as those exemplified for the compound [I].

Suitable reactive derivative at the carboxy or sulfo group of the compound [III]may include an ester, an acid halide, an acid anhydride and the like. The suitable examples of the reactive derivatives may be an acid halide [e.g. acid chloride, acid bromide, etc.]; a symmetrical acid anhydride; a mixed acid anhydride with an acid such as aliphatic carboxylic acid [e.g. acetic acid, pivalic acid, etc.]. substituted phosphoric acid [e.g. dialkyl-phosphoric acid, di-phenylphosphoric acid, etc.]; an ester such as substituted or unsubstituted lower alkyl ester [e.g. methyl ester, ethyl ester, propyl ester, hexyl ester, trichloromethyl ester, etc.], substituted or unsubstituted ar(lower)alkyl ester [e.g. benzyl ester, benzhydryl ester, p-chlorobenzyl ester, etc.], substituted or unsubstituted aryl ester [e.g. phenyl ester, tolyl ester, 4-nitrophenyl ester, 2,4-dinitrophenyl ester, pentachlorophenyl ester, naphthyl ester, etc.], or an ester with N,N-dimethylhydroxylamine, N-hydroxysuccinimide, N-hydroxythalimide or 1-hydroxy-6-chloro-1H-benzotriazole, or the like. These reactive derivatives can be optionally selected according to the kind of the compound [III] to be used.

The reaction is usually carried out in a conventional solvent such as water, acetone, dioxane, chloroform, methylene chloride, ethylene chloride, tetrahydrofuran, ethyl acetate, N,N-dimethylformamide, pyridine or any other organic solvent which does not adversely influence the reaction. Among these solvents, hydrophilic solvent may be used in a mixture with water.

When the compound [III] is used in a free acid form or its salt form in the reaction, the reaction is preferably carried out in the presence of a conventional condensing agent such as N,N'-dicyclohexylcarbodiimide, N-cyclohexyl-N'-morpholinoethylcarbodyimide, N-ethyl-N'-(3-dimethylaminopropyl)carbodiimide, thionyl chloride, oxalyl chloride, lower alkoxycarbonyl halide [e.g. ethyl chloroformate, isobutyl chloroformate, etc.], 1-(p-chlorobenzenesulfonyloxy)-6-chloro-1H-benzotriazole, or the like.

The reaction temperature is not critical, and the reaction can be carried out under cooling to heating.

Process 2

The compound [Ia] or its salt can be prepared by reacting a compound [II] or its salt with a compound [IV].

Suitable salts of the compound [II] may be the same as those exemplified for the compound [I].

This reaction is usually carried out in a solvent such as dioxane, tetrahydrofuran, benzene, chloroform, methylene chloride or any other organic solvent which does not adversely influence the reaction.

The reaction temperature is not critical, and the reaction is usually carried out under cooling to warming.

Process 3

The compound [Ic] can be prepared by reacting a compound [Ib] or its salt with a compound [V].

Suitable salts of the compound [Ib] may be the same as those exemplified for the compound [I].

The present reaction is preferably carried out in the presence of base such as an alkali metal (e.g. lithium, sodium, potassium, etc.), alkaline earth metal (e.g. calcium, etc.), alkali metal hydride (e.g. sodium hydride, etc.), alkaline earth metal hydride (e.g. calcium hydride, etc.) and the like.

This reaction is usually carried out in a solvent such as N,N-dimethylformamide, diethyl ether, tetrahydrofuran, dioxane, benzene, toluene or any other solvent which does not adversely influence the reaction.

The reaction temperature is not critical, and the reaction is usually carried out under cooling to heating.

The compounds obtained by the above processes can be isolated and purified by a conventional method such as pulverization, recrystallization, column chromatography, reprecipitation, or the like.

The object compounds [I] and pharmaceutically acceptable salts thereof possess strong potentiation of the cholinergic activity, and are useful for the treatment of disorders in the central nervous system for human beings, and more particularly of amnesia, dementia, senile deentia and the like.

In order to illustrate the usefulness of the object compound [I], the pharmacological test data of the compound [I] are shown in the following.

Anti-scopolamine-induced amnesia activity

Test Method :

Male Wistar rats (body weight 250–300 g, 23–31 per group) were used. The effect of the test compound on deficit of memory induced by scopolamine (a muscarinic acetylcholine receptor antagonist) in passive avoidance task was examined. The apparatus consists of an illuminated compartment attached to a dark compartment equipped with a grid floor. These compartments are separated with a guillotine door. The rat was placed in the illuminated compartment and 10 seconds after placing the rat, the guillotine door was raised. After the rat entered into the dark compartment, the rat was returned to its home cage (Habituation). 30 minutes after habituation, scopolamine hydrobromide (1 mg/kg) (Sigma Co. St Louis, MO, U.S.A.) was intraperitoneally (i.p.) administered. 60 minutes after habituation, the acquisition trial was carried out. The rat was again placed in the illuminated chamber. When the rat entered in the dark chamber, the quillotine door was closed and a 4mA scrambled electrical footshock was delivered for 3 seconds through the grid floor. Test compounds were intraperitoneally administered immediately after this training.

In the test trial given 24 hours after the training, the rat was placed again in the illuminated compartment and the response latency to enter into the dark compartment was measured to an extent of 300 seconds at the longest. Results were recorded as the mean latency of step through for each experimental group of rates. The effect of the test compound was presented as a percentage of the recovery. The calculation was based on the following equation.

$$\text{Percentage of Recovery (\%)} = \frac{A - B}{300 - B} \times 100$$

$A$: mean latency of test compound (sec)

$B$: mean latency of vehicle (sec)

Test Compounds:
(a) N-(4-Acetyl-1-piperazinyl)-4-fluorobenzamide
(b) N-(4-Benzoyl-1-piperazinyl)-4-fluorobenzamide
(c) N-(4-Acetyl-1-piperazinyl)-4-fluorobenzenesulfonamide Test Results:

| | Percentage of Recovery (%) | | |
| --- | --- | --- | --- |
| | Test Compound | | |
| Dose (mg/kg) | (a) | (b) | (c) |
| 0 | 0 | 0 | 0 |
| 0.1 | 23.0 | 26.4 | 20.4 |
| 0.32 | 24.6 | 29.5 | 26.8 |
| 1.0 | 40.3 | 19.7 | 34.5 |
| 3.2 | 39.2 | 41.5 | 50.2 |

For therapeutic purpose, the compound [I] and a pharmaceutically acceptable salt thereof of the present invention can be used in a form of pharmaceutical preparation containing one of said compounds, as an active ingredient, in admixture with a pharmaceutically acceptable carrier such as an organic or inorganic solid or liquid excipient suitable for oral, parenteral or external administration. The pharmaceutical preparations may be capsules, tablets, dragees, granules, solution, suspension, emulsion, or the like. If desired, there may be included in these preparations, auxiliary substances, stabilizing agents, wetting or emulsifying agents, buffers and other commonly used additives.

While the dosage of the compound [I] will vary depending upon the age and condition of the patient, an average single dose of about 0.1 mg, 1 mg, 10 mg, 50 mg, 100 mg, 250 mg, 500 mg and 1000 mg of the compound [I] may be effective for treating the above-mentioned diseases. In general, amounts between 0.1 mg/body and about 1,000 mg/body may be administered per day.

The following Preparations and Examples are given for the purpose of illustrating this invention.

Preparation 1

To a mixture of 1-nitrosopiperazine (1.21 g) and pyridine (2.4 ml) in dioxane (18 ml) was added dropwise 2-thenoyl chloride (1.2 ml) in an ice bath. The mixture was stirred for one hour in an ice.bath and then overnight at ambient temperature. The mixture was poured into a mixture of ethyl acetate (100 ml) and water (100 ml). The separated aqueous layer was extracted twice with ethyl acetate. The combined organic layers were dried and concentrated in vacuo. The residue was pulverized with diisopropyl ether to yield 1-nitroso-4-(2-thenoyl)-piperazine (1.78 g).

To a solution of 1-nitroso-4-(2-thenoyl)piperazine (1.78 g) in a mixture of acetic acid (8 ml) and water (8 ml) was added Zn powder (1.55 g) in several portions at 6°–15° C. The suspension was stirred for 1.5 hours below 10° C. To the mixture was added acetic acid (4 ml) and Zn powder (780 mg) at 8°–12° C. The mixture was stirred for 2 hours at ambient temperature. To the suspension was added 17% aqueous sodium hydroxide solution (70 ml). The insoluble materials were filtered off. The aqueous layer was extracted with dichloromethane. The combined organic layers were dried and concentrated in vacuo. The residue was purified by column chromatography on silica gel (elution by 5% methanol in dichloromethane) to yield 1-amino-4-(2-thenoyl)piperazine (1.17 g) as a pale yellow syrup.

$^1$H NMR (CDCl$_3$, δ) : 7.48 (1H, dd, J=1 and 5Hz), 7.31 (1H, dd, J=1 and 4Hz), 7.07 (1H, dd, J=4 and 5Hz), 3.83 (4H, t, J=5Hz), 2.88 (2H, br.s), 2.70 (4H, t, J=5Hz)

The following compound (Preparation 2) was obtained according to a similar manner to that of Preparation 1.

Preparation 2

1-Amino-4-(2-naphthoyl)piperazine pale yellow syrup $^1$H NMR (CDCl$_3$, δ) : 7.98–7.83 (4H, m), 7.65–7.45 (3H, m), 3.88 (2H, br.s), 3.62 (2H, br.s), 3.04 (2H, br.s), 2.68 (4H, br.s)

Preparation 3

To a solution of 1-[2-[bis(4-fluorophenyl)-methoxy]ethyl]piperazine (1 g) in 1N-hydrochloric acid (3 ml) was added 1N-hydrochloric acid in order to adjust pH to 4. The mixture was stirred at 70°–75° C. and therein a solution of sodium nitrite (0.31 g) in water (0.5 ml) was added dropwise. The mixture was stirred at 70°–75° C. for one hour, cooled, and diluted with a mixture of diethyl ether and aqueous sodium bicarbonate solution. The organic layer was washed withbrine, dried, and concentrated in vacuo. The residue was purified by column chromatography on silica gel eluted with chloroform to yield 1-[2-[bis(4-fluorophenyl)methoxy]ethyl]-4-nitrosopiperazine (0.9 g) as an oil.

$^1$H NMR (CDCl$_3$, δ) : 7.28 (4H, dd, J=5 and 9Hz), 7.02 (4H, t, J=9Hz), 5.36 (1H, s), 4.28 (2H, t, J=6Hz), 3.93–3.77 (2H, m), 3.62 (2H, t, J=6Hz), 2.84–2.67 (4H, m), 2.58–2.43 (2H, m)

Preparation 4

To a solution of 1-[2-[bis(4-fluorophenyl)methoxy]ethyl]-4-nitrosopiperazine (0.9 g) in a mixture of acetic acid (2.4 ml) and water (1.2 ml) was added Zn powder (0.75 g) in several portions below 10° C. After stirring for an hour below 10° C., the mixture was further stirred for four hours at ambient temperature. The insoluble materials were removed by filtration and the filtrate was saturated with hydrogen sulfide. The precipitate was filtered off and the filtrate was concentrated in vacuo. The residue was dissolved with chloroform, washed with saturated aqueous solution of sodium hydrogen carbonate and dried over sodium sulfate. After evaporation of the solvent, 1-amino-4-[2-[bis(4-fluorophenyl)methoxy]ethyl]piperazine as an oil.

$^1$H NMR (CDCl$_3$, δ) : 7.28 (4H, dd, J=5 and 9Hz), 7.00 (4H, t, J=9Hz), 5.32 (1H, s), 3.53 (2H, t, J=6Hz), 2.90–2.30 (12H, m)

EXAMPLE 1

To a mixture of 1-acetyl-4-aminopiperazine dihydrochloride (540 mg) and 4-fluorobenzenesulfonyl chloride (535 mg) in dichloromethane (5 ml) was added triethylamine (1.2 ml) in a few minutes with stirring in an ice bath. After stirring for half an hour at the same temperature, the mixture was washed with brine, dried, and concentrated in vacuo. The residue was crystallized from ethanol and recrystallized from a mixture of ethanol and diethyl ether to Yield N-(4-acetyl-1-piperazinyl)-4-fluorobenzenesulfonamide (360 mg) as white crystals.

mp : 185°–186° C.

IR (CHCl$_3$) : 3400, 3300, 3005, 1642, 1638, 1596, 1498, 1460, 1256, 1240, 1170, 1155, 1094 cm$^{-1}$

EXAMPLE 2

To a solution of 1-amino-4-benzylpiperazine (1.1 g) and triethylamine (0.6 g) in dichloromethane (20 ml) was added dropwise 4-fluorobenzoyl chloride (0.86 g) with stirring in an ice bath. After stirring for one hour at the same temperature, the mixture was washed with 1N hydrochloric acid, dried, and concentrated in vacuo. The residue was crystallized from diisopropyl ether and purified by recrystallization from ethanol to give N-(4-benzoyl-1-piperazinyl)-4-fluorobenzamide (0.97 g) white crystals. m.p.:

206°–207° C.

$^1$H NMR (CDCl$_3$, δ) : 7.78 (2H, dd, J=5 and 9Hz), 7.43 (5H, s), 7.34 (1H, br.s), 7.12 (2H, t, J=9Hz), 3.96 (2H, br.s), 3.67 (2H, br.s), 3.03 (4H, br.s)

The following compound (Example 3) was obtained according to a similar manner to that of Example 1.

Example 3

N-(4-Benzenesulfonyl-1-piperazinyl)-4-fluorobenzenesulfonamide mp : 190°–191° C.

$^1$H NMR (CDCl$_3$-CD$_3$OD=1:1, δ) : 7.88 (2H, dd, J=5 and 9Hz), 7.78–7.57 (5H, m), 7.20 (2H, t, J=9Hz), 3.03–2.92 (4H, m), 2.75–2.66 (4H, m)

The following compounds (Examples 4-1) to 4-11)) were obtained according to a similar manner to that of Example 2.

Example 4

1) N-(4-Acetyl-1-piperazinyl)-2-fluorobenzamide
mp : 171°–172° C.

IR (CHCl$_3$) : 3480, 3400, 3015, 1678, 1644, 1619, 1488, 1458, 1444, 1300, 1285, 1262 cm$^{-1}$

2) N-(4-Acetyl-1-piperazinyl)-3-fluorobenzamide mp : 196°–197° C.

IR (CHCl$_3$) : 3350, 3005, 1680, 1640, 1592, 1440, 1282, 1258 cm$^{-1}$

3) N-(4-Acetyl-1-piperazinyl)-4-fluorobenzamide mp : 211°-212° C.

$^1$H NMR (DMSO- d$_6$) : 9.58 (1H, s), 7.84 (2H, dd, J=6 and 9Hz), 7.31 (2H, t, J=9Hz), 3.52 (4H, t, J=6Hz), 2.88 (2H, t, J=6Hz), 2.82 (2H, t, J=6Hz), 2.03 (3H, s)

4) N-(4-Acetyl-1-piperazinyl)cyclohexanecarboxamide mp : 220°-221° C.

IR (CHCl$_3$) : 3430, 3340, 2998, 2940, 2852, 1638, 1448, 1280, 1256, 1140, 1118, 998 cm$^{-1}$

5) N-(4-Acetyl-1-piperazinyl)-4-fluorophenylacetamide mp : 163°-164° C.

IR (CHCl$_3$) 3440, 3340, 3300, 1670, 1640, 1510, 1440, 1282, 1258, 1158, 1140, 1120, 1000 cm$^{-1}$

6) N-(4-Phenylsulfonyl-1-piperazinyl)-4-fluorobenzamide mp : 274°-276° C.

$^1$H NMR (CDCl$_3$-CD$_3$OD =1:1, δ) : 7.86-7.58 (7H, m), 7.14 (2H, t, J=9Hz), 3.28-3.18 (4H, m), 3.07-2.98 (4H, m)

7) N-(4-Methylsulfonyl-1-piperazinyl)-4-fluorobenzamide mp : 257°-258° C.

$^1$H NMR (CDCl =1:1, 6) : 7.80 (2H, dd, J=5 and 9Hz), 7.12 (2H, t, J=9Hz), 3.40 (4H, t., J=5Hz), 2.99 (4H, t, J=5Hz), 2.88 (3H, s)

N-[4-(2-Thenoyl)-1-piperazinyl]-4-fluorobenzamide
mp : 189°-190C.

IR (CHCl$_3$) : 3440, 3340, 3280, 3000, 1674, 1604, 1501, 1438, 1284, 1259 cm.$^{-1}$

9) N-[4-(2-Naphthoyl)-1-piperazinyl]-4-fluorobenzamide mp 227°-228° C.

IR (CHCl$_3$) : 3430, 3335, 2990, 1668, 1617, 1601, 1496, 1477, 1438, 1284, 1260 cm$^{-1}$

(10) N-(4-Benzyl-1-piperazinyl)-4-fluorobenzamide
mp : 165°-168° C.

$^1$H NMR (CDCl$_3$, δ) : 7.77 (2H, dd, J=5 and 9Hz), 7.45-7.23 (5H, m), 7.10 (2H, t, J=9Hz), 3.41 (2H, s), 3.00 (4H, br.s), 2.72 (4H, br.s)

11) N-[4-[2-[Bis(4-fluorophenyl)methoxy]ethyl]-1-piperazinyl]-4-fluorobenzamide mp : 141°-144° C.

$^1$H NMR (CDCl$_3$, δ) : 7.88-7.70 (2H, m), 7.28 (4H, dd, J=5 and 9Hz), 7.20-6.95 (6H, m), 6.90 (1H, s), 5.35 (1H, s), 3.60 (2H, t, J=6Hz), 3.10-2.60 (10H, m)

Example 5

To a solution of 1-acetyl-4-aminopiperazine dihydrochloride (540 mg) in dichloromethane (5 ml) was added dropwise triethylamine (0.8 ml) followed by addition a solution of 4-fluorophenylisocyanate (377 mg) in dichloromethane (2.5 ml) with stirring in an ice bath. After stirring for 100 minutes at the same temperature, a mixture of dichloromethane (15 ml) and methanol (3 ml) was added to the reaction mixture. The mixture was washed with brine, dried, and concentrated in vacuo. The residue was crystallized from ethanol to yield N-(4-acetyl-1-piperazinyl)-N'-(4-fluoroph-enyl)urea (500 mg).

mp : 210°-211° C.

$^1$H NMR (CDCl$_3$, δ) : 7.98 (1H, s), 7.40 (2H, dd, J=5 and 9Hz), 7.00 (2H, t, J=9Hz), 5.88 (1H, br.s), 3.80-2.50 (8H, m), 2.14 (3H, s)

Example 6

To a solution of N-(4-acetyl-1-piperazinyl)-4-fluorobenzadide (769 mg) in N,N-dimethylformamide (8 ml) was added sodium hydride (116 mg, 60% oil dispersion) in one portion with stirring in an ice bath. The mixture was stirred for one hour at the same temperature and therein iodomethane (0.3 ml) was added. After stirring for one hour in an ice bath, the mixture was concentrated in vauco. The residue was purified by column chromatography on Dowex (50W ×8$^+$) to give N-(4-acetyl-1-piperazinyl)-N-methyl-4-fluorobenzamide (440 mg).

mp : 205°-206° C.

IR (CHCl$_3$) : 3010, 2960, 1652, 1612, 1570, 1508, 1440, 1440, 1344, 1268, 1154 cm$^{-1}$

What we claim is:

1. A compound of the formula:

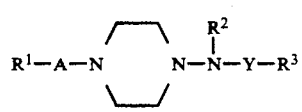
[I]

wherein
R$^1$ is lower alkyl, phenyl, naphthyl, tolyl, xylyl, mesityl, cumenyl or thienyl,
R$^2$ is hydrogen or lower alkyl,
R$^3$ is cyclo(lower)alkyl or phenyl, each of which may be substituted with halogen,
A is

and
Y is

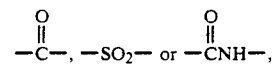

or pharmaceutically acceptable salts thereof.

2. A compound according to claim 1,
wherein
R$^1$ is lower alkyl, phenyl, naphthyl or thienyl, and
R$^3$ is phenyl which may be substituted with halogen.

3. A compound according to claim 2,
wherein
R$^2$ is hydrogen,
R$^3$ is phenyl which is substituted with halogen, and
Y is

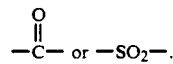

4. A compound of claim 3, which is N-(4-acetyl-1-piperazinyl)-4-fluorobenzamide.

5. A compound of claim 3, which is N-(4-benzoyl-1-piperazinyl)-4-fluorobenzamide.

6. A compound of claim 3, which is N-(4-acetyl-1-piperazinyl)-4-fluorobenzenesulfonamide.

7. A pharmaceutical composition comprising a compound of claim 1, as an active ingredient, in association with a pharmaceutically acceptable, substantially nontoxic carrier or excipient.

8. A method for therapeutic treatment of amnesia which comprises administering an effective amount of a compound of claim 1 to a human being.

* * * * *

UNITED STATES PATENT AND TRADEMARK OFFICE
CERTIFICATE OF CORRECTION

PATENT NO. : 5,250,528
DATED : October 5, 1993
INVENTOR(S) : Teruo Oku et al.

It is certified that error appears in the above-indentified patent and that said Letters Patent is hereby corrected as shown below:

On the title page, Item [30],

The Foreign Application Priority Data, please insert:

--Jul. 12, 1990 [PCT] PCT......................PCT/JP90/00898--

Signed and Sealed this

Twentieth Day of June, 1995

*Attest:*

BRUCE LEHMAN

*Attesting Officer*  *Commissioner of Patents and Trademarks*